(12) United States Patent
Bakhit et al.

(10) Patent No.: US 7,244,768 B2
(45) Date of Patent: Jul. 17, 2007

(54) COMPOSITIONS AND METHODS COMPRISING PROSTAGLANDIN RELATED COMPOUNDS AND TREFOIL FACTOR FAMILY PEPTIDES FOR THE TREATMENT OF GLAUCOMA WITH REDUCED HYPEREMIA

(75) Inventors: Peter G. Bakhit, Huntington Bech, CA (US); Richard Graham, Irvine, CA (US); Orest Olejnik, Coto De Caza, CA (US)

(73) Assignee: Allergan, Inc., Irvine, CA (US)

( * ) Notice: Subject to any disclaimer, the term of this patent is extended or adjusted under 35 U.S.C. 154(b) by 352 days.

(21) Appl. No.: 10/521,367

(22) PCT Filed: Aug. 25, 2004

(86) PCT No.: PCT/US2004/027777

§ 371 (c)(1),
(2), (4) Date: Jan. 12, 2005

(87) PCT Pub. No.: WO2005/039619

PCT Pub. Date: May 6, 2005

(65) Prior Publication Data

US 2006/0046958 A1    Mar. 2, 2006

Related U.S. Application Data

(60) Provisional application No. 60/508,445, filed on Oct. 3, 2003.

(51) Int. Cl.
*A61K 31/165* (2006.01)
*A61K 31/00* (2006.01)

(52) U.S. Cl. ........................................ 514/623; 514/13

(58) Field of Classification Search ................ 514/623, 514/13
See application file for complete search history.

(56) References Cited

U.S. PATENT DOCUMENTS 5,688,819 A    11/1997    Woodward et al.
6,525,018 B1 *    2/2003    Podolsky ...................... 514/2
6,984,628 B2 *    1/2006    Bakhit et al. ................ 514/21
7,074,827 B2 *    7/2006    Ueno .......................... 514/530

FOREIGN PATENT DOCUMENTS

WO    WO 02102403    12/2002

OTHER PUBLICATIONS

Sharif et al., Ocular Hypotensive FP Prostaglandin (PG) Analogs: PG Receptor Subtype Binding Affinities and Selectivities, and Agonist Potencies at FP and Other PG Receptors in Cultured Cells, Dec. 2003, Journal of Ocular Pharmacology and Therapeutics, vol. 19, No. 6, pp. 501-515.*

Tan et al., "Prostanoids mediate the protective effect of trefoil fact 3 in oxidant-induced intestinal epithelial cell injury: role of cyclogenase-2", Journal of Cell Science, 2000, vol. 113, pp. 2149-2155.*

Ghelardi et al., "Effect of a novel mucoadhesive polysccharide obtained from tamarind seeds on the intraocular penetration of gentamicin and ofloxacin in rabbits", J. Antimicrob Chemother, Nov. 2000;46(5), pp. 831-834.*

Francis A. Carey, Organic Chemistry, New York: McGraw-Hill Book Company, 1987, 778.

Bezuglov et al, "Synthesis and Biological Evaluation of Novel Amides of Polyunsaturated Fatty Acids with Dopamine", Biorganic & Medicinal Chemistry Letters 11 (2001), 447-449.

Hauser et al, "hP1.B, a human P-domain peptide homologous with rat intestinal trefoil factor, is expressed also in the ulcer-associated cell lineage and the uterus", Proc Natl Acad Sci USA, 1993, vol. 90, 6961-6965.

Babyatsky et al, "Oral Trefoil Peptides Protect Against Ethanol- and Indomethacin-Induced Gastric Injury in Rats", Gastroenterology, 1996, vol. 110, 489-497.

Goke et al, "Trefoil Peptides Promote Restitution of Wounded Corneal Epitheal Cells", Experimental Cell Research, 2001, vol. 264, 337-344.

Playford, Trefoil peptides: what are they and what do they do?? Journal of the Royal College of Physicians of London, vol. 31, 37-40.

Langer et al, "Secretory Peptides TFF1 and TFF3 Synthesized in Human Conjunctival Goblet Cells", Invest Ophthalmol Vis Sci., 1999, vol. 40, 2220-2224.

Allen et al, "Its Role in Gastroduodenal Mucosal Protection", J. Clin Gastronenterol, 1998; 10(Suppl 1):S93-S98.

Ligumsky et al, "Sucralfate Protection Against Gastrointestinal Damage: Possible Role of Prostanoids", Israel J. Med Sci 1986, 22: 801-806.

Dignass et al, "Trefoil Peptides Promote Epithelial Migration through a Transforming Growth Factor β-independent Pathway", J. Clin. Invest., 94, 376-383.

Tabor et al, "Surface Forces and Surface Interactions", 1977, J. Colloid Interface Sci. 58: 2-13.

Good, "Surface Free Energy of Solids and Liquids: Thermodynamics, Molecular Forces, and Structure", Journal of Collioid Interface Sci., 1977, 59:398.

* cited by examiner

*Primary Examiner*—Cecilia Tsang
*Assistant Examiner*—GiGi Huang
(74) *Attorney, Agent, or Firm*—Brent A. Johnson; Martin A. Voet

(57) ABSTRACT

Compositions, methods, and pharmaceutical products related to prostaglandin-related compounds and trefoil factor family peptides are disclosed herein. Of particular interest are compositions and methods useful for the treatment of glaucoma with a reduced occurrence of hyperemia.

14 Claims, No Drawings

COMPOSITIONS AND METHODS COMPRISING PROSTAGLANDIN RELATED COMPOUNDS AND TREFOIL FACTOR FAMILY PEPTIDES FOR THE TREATMENT OF GLAUCOMA WITH REDUCED HYPEREMIA

CROSS REFERENCE TO RELATED APPLICATIONS

This is a national stage application under 35 U.S.C. § 371 of PCT application PCT/US2004/02777, filed on Aug. 25, 2004, which claims the benefit of Provisional Application No. 60/508,445, filed on Oct. 3, 2003.

FIELD OF THE INVENTION

The present invention relates to pharmaceutical compositions comprising prostaglandin-related compounds and trefoil factor family peptides.

BACKGROUND OF THE INVENTION

Description of Related Art

Active drugs often have undesirable side effects at their therapeutically effective concentrations. This is particularly problematic for topical use in sensitive areas such as the eyes, where irritation is very difficult to avoid even for relatively mild drugs. As a result, formulating topical ophthalmic drugs is a particularly challenging problem. This is unfortunate because topical ophthalmic use of drugs has been found to be very useful in managing many conditions affecting the eye such as dry eye, infection, inflammation, allergy, and glaucoma. Glaucoma is a particularly devastating disease of the eye characterized by increased intraocular pressure, which is often treated by topical ophthalmic application of a drug. Glaucoma occurs in about 2% of all persons over the age of 40 and may be asymptotic for years before progressing to rapid loss of vision. In cases where surgery is not indicated, many drugs have been found to be useful in treating glaucoma by topical application including β-adrenoreceptor antagonists and $α_2$-adrenoreceptor agonists. Recently, prostaglandins have been shown to be particularly useful in the topical treatment of glaucoma.

Whereas prostaglandins appear to be devoid of significant intraocular side effects, ocular surface (conjunctival) hyperemia, foreign-body sensation, and itching (pruritus) have been consistently associated with the topical ocular use of such compounds, in particular $PGF_{2α}$ and its prodrugs, e.g., its 1-isopropyl ester, in humans. The clinical potentials of prostaglandins in the management of conditions associated with increased ocular pressure, e.g. glaucoma are greatly limited by these side effects.

U.S. Pat. No. 5,688,819, commonly assigned to Allergan, Inc., and incorporated herein by reference discloses compounds known as prostamides. Prostamides are distinguished from prostaglandins in that the oxygen which is bonded to carbonyl group is replaced by a nitrogen bearing substituent. Those skilled in the art will readily recognize that this replacement significantly alters several electronic and steric properties of an important structural feature in the biological molecule. Significantly, it is commonly believed in the art that resonance between the nitrogen lone pair and the carbonyl π-bond is significantly greater than resonance between the carbonyl group and an oxygen lone pair in a carboxylic ester or a carboxylic acid. This belief is supported by the well established experimental observation that the nitrogen atom in an amide is planar, as opposed to the pyramidal geometry of an amine. Thus, the commonly accepted belief in the art is that the nitrogen atom of an amine is $sp^3$ hybridized, while nitrogen atom of an amide is $sp^2$ hybridized, with the bonded electrons occupying the $sp^2$ hybrid orbitals and the nonbonded electron pair occupying a p orbital to allow for conjugation with the carbonyl π system. By contrast, the hybridization, bonding, and geometry of the electrons of the oxygen atom in water and alcohols are very similar to those of carboxylic acids or carboxylic esters.

The increased resonance between the nitrogen and the carbonyl group in the amide confers several unique properties to the molecule. First, it is well known in the art that hydrolysis of amides is at least two orders of magnitude slower than the hydrolysis of esters (see, for example, Francis A. Carey, Organic Chemistry, New York: McGraw-Hill Book Company, 1987, p. 779). Thus, hydrolysis of amides in vivo is slowed to such an extent that a prostamide cannot be considered to be a prodrug of a prostaglandin. Second, the increased resonance significantly increases the barrier to rotation about the nitrogen-carbonyl sigma bond relative to the analogous rotational barrier associated with esters and carboxylic acids. Thus, a prostamide has a sterically significant, stable, rigid group replacing the oxygen atom of the prostaglandin. This significant steric difference will have a significant effect in binding to a number of receptor sites since geometry is important for many receptor sites. Since the carboxylic acid group of a prostaglandin is a polar, ionizable, group, with four potential hydrogen bond receiving electron pairs, and in the case of the protonated acid, one potential hydrogen bond donor, it is reasonable for a person of ordinary skill in the art to believe that this functional group will be important to the binding of the molecule to a number of receptors. It follows that changing the resonance properties, the hybridization of the bonding and nonbonding electrons, the geometry of the nitrogen atom, the number of available hydrogen bonding sites, and the electronegativity of the of the nitrogen relative to oxygen, will confer significantly different biological properties to prostamides relative to prostaglandins.

Recently, it is becoming more commonly accepted in the art that amides have distinct properties over carboxylic acids. For example, it has been shown that anandamide, a common amide of arachidonic acid, has significant biological activity that arachidonic acid does not. Other work has also been done to show that amides have distinct activity as compared to carboxylic acid, which has caused some in the field to classify fatty acid amides as "a new family of biologically active lipids" (Bezuglov, et. al., "Synethesis and Biological Evaluation of Novel Amides of Polyunsaturated Fatty Acids with Dopamine", Bioorganic & Medicinal Chemistry Letters 11 (2001), 447-449).

It has been shown that prostamides have pronounced effects on smooth muscle and are potent ocular hypotensive agents. Additionally, prostamides cause significantly lower ocular surface hyperemia than prostaglandins. One prostamide exemplary of the these effects is bimatoprost, which is marketed by Allergan, Inc. under the trade name Lumigan®, which has the structure shown in Formula I below.

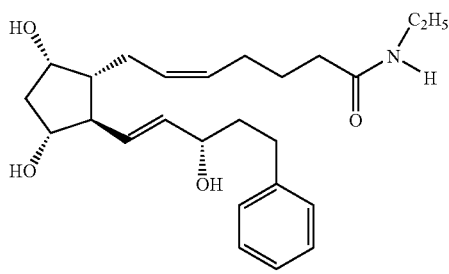

Formula I

However, although bimatoprost is associated with significantly less hyperemia and other irritating side effects compared to certain prostaglandins, further improvement is still highly desirable.

Trefoil peptides, or trefoil factor family (TFF) peptides are a class of peptides which comprise a common structural motif, known as the trefoil domain, as part of their structure. The trefoil motif comprises about 20 to about 60 amino acid residues (usually about 40) containing six cysteine residues. The six cysteine residues form three disulfide bridges that complete three loops in the peptide chain so that the roughly 40 residues have a clover-like shape, known as the trefoil domain. TFF-peptides can have one or two trefoil domains per molecule, and may comprise additional amino acid residues which are not part of the trefoil domain. To date, three types of TFF-peptides have been isolated from humans-TFF1 (also known as pS2), TFF2 (also known as SP), and TFF3 (also known as ITF). TFF1 and TFF3 peptides each contain one trefoil domain, while TFF2 peptides contain two trefoil domains. TFF1 and TFF2 peptides are both produced by mucus-producing cells of stomach, while TFF3 peptides are produced by goblet cells of small and large intestine.

All three forms of TFF-peptides are known to be produced in epithelial cells around areas of damage to mucus membrane, suggesting that trefoils have a role in healing injury, particularly to epithelial cells. It is believed that TFF-peptides assist healing by both stabilizing mucus membrane at the injury site and by stimulating repair. It has been shown that TFF-peptides noncovalently link mucin, thus influencing the rheology (e.g. increases viscosity) of mucus gels. [Hauser F, Poulsom R, Chinery R, et al, *Proc Natl Acad Sci USA*, 1993, vol. 90, pp. 6961-6965; and Babyatsky M W, deBeaumont M, Thim L, Podolky D K, *Gastroenterology*, 1996, vol. 110, pp. 489-497]. TFF-peptides also appear to be responsible for promoting the migration of epithelial cells to the site of injury, thus stimulating repair. [Göke M, et al, *Experimental Cell Research*, 2001, vol 264, pp. 337-344; and Playford R J, Journal of the Royal College of Physicians of London, vol 31, pp. 37-40].

Although there is still a great deal unknown about the role of TFF peptides on the ocular surface, in the lacrimal gland, in the efferent passages, and in surrounding tissue, it is believed that TFF-peptides may be present during healing and other related processes in the eye. Biosynthesis and storage TFF1 and TFF3 peptides, but not TFF2, is known to occur in the human conjunctival epithelium [Langer G, et al, *Invest Ophthalmol Vis Sci*, 1999, vol. 40, pp. 2220-2224], and in vitro studies have shown that TFF2 and TFF3 peptides promote the migration of wounded corneal epithelial-cells from rabbits [Göke M, et al, *Experimental Cell Research*, 2001, vol 264, pp. 337-344]. However, to the best of our knowledge, no direct relationship has been unambiguously established between TFF-peptides and any pathological condition affecting the eye.

SUMMARY OF THE INVENTION

Disclosed herein are dosage forms and methods which comprise a prostaglandin or a prostamide and a trefoil factor family peptide.

DETAILED DESCRIPTION OF THE INVENTION

Disclosed herein are dosage forms which comprise a prostaglandin or a prostamide and a trefoil factor family peptide. Also disclosed are methods of treating ocular or conjunctival hyperemia in a person comprising administering topically to an eye of said person a therapeutically effective amount of a trefoil factor family peptide, wherein said person is being treated for glaucoma with a prostaglandin-related compound.

In relation to the methods disclosed herein, the individual properties of the prostaglandin-related compound and the trefoil factor family peptide may be considerations in determining how the two are administered. In certain embodiments the prostaglandin-related compound and trefoil factor family are administered in a single composition. In other embodiments, the prostaglandin-related compound and the trefoil factor family peptide are administered separately. In other embodiments, the prostaglandin-related compound and the trefoil factor family peptide are administered simultaneously. In other embodiments, the prostaglandin-related compound and the trefoil factor family peptide are administered at substantially different times. In other embodiments, the prostaglandin-related compound and the trefoil factor family peptide are administered with equal frequency. In other embodiments, the prostaglandin-related compound is administered more frequently than the trefoil factor family peptide. In other embodiments, the prostaglandin-related compound is administered less frequently than the trefoil factor family peptide.

A "prostaglandin-related compound" is broadly defined as any compound related to a prostaglandin by being a natural prostaglandin, a prostaglandin analog, a prostaglandin receptor agonist, a prostamide, or a pharmaceutically acceptable salt, or a prodrug of any of the previous classes. Natural prostaglandins can be described as derivatives of prostanoic acid which have the following structural formula:

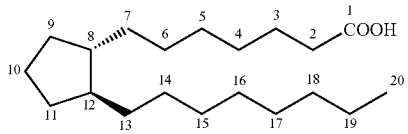

In relation to the structure above and prostaglandin-related compounds, term "α chain" refers to the top chain which is formed by the carbon atoms referred to as 1-7 in the structure above. The term "ω chain" refers to the bottom chain which is formed by the carbon atoms referred to as 13-20 in the structure above. The ring formed by the carbon atoms referred to as 8-12 will be referred to as the "cyclopentyl ring" herein for convenience. Natural prostaglandins are characterized by the presence of functional groups or double bonds on their cyclopentyl ring, and by the presence or absence of a cis double bond between carbons 5 and 6, and by the presence or absence of a trans double bond between carbons 13 and 14. Such nomenclature is well known in the art. However, while not desiring to limit the scope of the invention in any way, some important groups of natural prostaglandin compounds are prostaglandin E, prostaglandin F, and prostaglandin D. Prostaglandin E is characterized by a carbonyl group at carbon 9 and a hydroxyl group at carbon 11 which is in the alpha configuration. One prostaglandin E which is of interest herein is prostaglandin $E_1$, which has a single covalent bond between carbons 5 and 6 and a double covalent bond between carbons 13 and 14. Another prostaglandin E of interest herein is prostaglandin $E_2$, which has a double covalent bond between carbons 5 and 6 and a double covalent bond between carbons 13 and 14. Thus, the subscript designates the number of carbon-carbon double bonds found in the basic prostaglandin structure.

The compounds known collectively as prostaglandin F are characterized by the common features that both carbons 9 and 11 have hydroxyl groups attached. Similar to prostaglandin E the OH is in the α-configuration for carbon 11, but the configuration of the OH at carbon 9 is designated by a subscript. Thus, prostaglandin $F_{2\alpha}$, which is of particular interest herein, is a prostaglandin F which has the OH of carbon 9 in the α-configuration, and similar to prostaglandin $E_2$, prostaglandin $F_{2\alpha}$ has two double covalent carbon-carbon bonds between carbons 5 and 6 and carbons 13 and 14.

The compounds known collectively as prostaglandin D are characterized by the common features that carbon 9 is CHOH, where the OH is in the α-configuration, and carbon 11 is C=O. Similar to the previous examples, one prostaglandin D of interest herein is designated prostaglandin $D_2$, which indicates that the compound has two double covalent carbon-carbon bonds between carbons 5 and 6 and carbons 13 and 14.

A "prostaglandin analog" as used herein refers to a compound having certain structural similarities to the natural prostaglandins. An analog has all of the features of a natural prostaglandin related to the cyclopentyl ring, including stereochemistry, the α-hydroxyl group at C15, and the presence or absence of double bonds at carbons 5, 6, 13 and 14, or reasonable equivalents of those features. A reasonable equivalent to a feature is a feature that a person of ordinary skill in the art would reasonably consider as having a similar purpose, but might enhance the properties of the compound. While not intending to limit the scope of the invention in any way, in general, an atom or functional group which is isovalent or isoelectronic with the atom or functional group it is replacing would be a reasonable equivalent. Thus, for example, an α-CHSH group is a reasonable equivalent for an α-CHOH group, and a C=S group is a reasonable equivalent for a C=O group. Another type of reasonable equivalent has different electronic properties but similar steric properties to the group it is replacing. Thus, F is a reasonable equivalent for H and $OCH_3$ is a reasonable equivalent for OH.

Beyond the similarities for the cyclopentyl ring and the double bonds indicated, a prostaglandin analog will have an α-chain and an ω-chain which are attached to adjacent atoms on the cyclopentyl ring. The meanings of the cyclopentyl ring and the α and ω chains for prostaglandin analogs are broader than those of the natural prostaglandins. For a prostaglandin analog, the "cyclopentyl ring" is a five-membered ring consisting of three or more carbon atoms, the "α-chain" has between 4 and 12 carbon atoms and the "ω-chain" has between 4 and 20 carbon atoms. Either chain may comprise double or triple covalent bonds, aromatic or aliphatic rings, and heteroatoms such as S, O, N, and halogens. The only stereochemical requirements of prostaglandin analogs are the same as those of the natural prostaglandins they are associated with. Thus, for a prostaglandin E analog, carbon 9 and carbon 11 should be CHOH with the OH in the α-configuration, and the α- and ω-chains should have the α and β configurations respectively with relation to the connection to the cyclopentyl ring. The table below lists features which would be present in analogs of several types of natural prostaglandins. Alternatively, a reasonable equivalent for each feature might be present in the given prostaglandin analog.

| Prostaglandin Analog | C9 | C11 | C15 | C5–C6 | C13–C14 |
|---|---|---|---|---|---|
| E | C=O | CH(OH) α conf | CH(OH) α conf | NA | NA |
| $E_1$ | C=O | CH(OH) α conf | CH(OH) α conf | single bond | trans double bond |
| $E_2$ | C=O | CH(OH) α conf | CH(OH) α conf | cis double bond | trans double bond |
| F | CH(OH) | CH(OH) α conf | CH(OH) α conf | NA | NA |
| $F_{2\alpha}$ | CH(OH) α conf | CH(OH) α conf | CH(OH) α conf | cis double bond | trans double bond |
| D | CH(OH) α conf | C=O | CH(OH) α conf | NA | NA |
| $D_2$ | CH(OH) α conf | C=O | CH(OH) α conf | cis double bond | trans double bond |

NA means there is no requirement.

"A prostaglandin receptor agonist" refers to a compound which binds to and activates one of the prostaglandin receptors at a concentration of less than $10^4$ nanomolar according to the Radioligand Binding and the FLIPR™ assay described hereafter. Of particular interest herein are compounds having agonist activity at an FP receptor, an $EP_2$ receptor, an $EP_4$ receptor, and/or a DP receptor.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[³H-] PGE$_2$ (specific activity 180 Ci mmol) was used as the radioligand for EP receptors. [³H] 17-phenyl PGF$_{2\alpha}$ was employed for FP receptor binding studies. Binding studies employing EP$_1$, EP$_2$, EP$_4$ and FP receptors were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [³H]-PGE$_2$, or 5 nM [³H] 17-phenyl PGF$_{2\alpha}$ and non-specific binding determined with $10^{-5}$M of unlabeled PGE$_2$, or 17-phenyl PGF$_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3A}$/Gqi5; hEP$_4$/Gqs5; hFP; hIP; hTP), were cultured in 100 mm culture dishes in high-glucose DMEM medium containing 10% fetal bovine serum, 2 mM l-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates were washed four times with HBSS-HEPES buffer to remove excess dye leaving 100 µl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 µl volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_{3A}$/Gqi5; hEP$_4$/Gqs5); PGF$_{2\alpha}$ (hFP); carbacyclin (hIP); U46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

Prostamides are also considered to be "prostaglandin-related" compounds. For the purposes of this disclosure, the term amide has the broadest meaning generally understood by organic chemists. Prostamides are prepared by methods generally known in the art, and also by the methods described in U.S. Pat. No. 5,688,819, incorporated herein by reference. One important embodiment relates to the use of bimatoprost in the compositions and methods disclosed herein. Bimatoprost is marketed under the tradename Lumigan® by Allergan, Inc.

The term "prodrug" used herein has the meaning normally understood in the art. That is, the prodrug is a compound which readily decomposes in vivo to form a natural prostaglandin, a prostaglandin analog, a prostamide or a prostaglandin receptor agonist. While not intending to limit the scope of the invention in any way, one common type of prodrug is an ester which hydrolyzes to yield an active compound with a hydroxide functional group.

The term "salt" has the meaning normally understood by those of ordinary skill in the art. A "pharmaceutically acceptable salt" is any salt that retains the activity of the parent compound and does not impart any deleterious or untoward effect on the subject to which it is administered and in the context in which it is administered.

Pharmaceutically acceptable salts of acidic functional groups may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Certain terminology is used to refer to particular prostaglandin-related classes of compounds. A compound which is referred to as "prostaglandin F-related" is a natural prostaglandin F, a prostaglandin F analog, a prostaglandin FP receptor agonist, or a prostamide having the characteristic features of prostaglandin F analog as described previously, or a salt or a prodrug of any of the previous classes of compounds. Similar terminology can be used to identify other prostaglandin compounds related to different classes of prostaglandins such as prostaglandin E ("prostaglandin E-related") or prostaglandin D ("prostaglandin D-related").

The quantity or concentration of a prostaglandin-related compound to be used in the compositions and methods disclosed herein can be determined by one of ordinary skill in the art without undue experimentation. In one embodiment, the concentration of the prostaglandin-related compound in the dosage form in which it is administered is from 0.001% to 0.1%. In another embodiment, the concentration of the prostaglandin-related compound in the dosage form in which it is administered is about 0.03%.

The term trefoil factor family (TFF) peptide as used herein refers to any peptide, whether natural or synthetic, which comprises the trefoil motif described previously herein. That is, the TFF-peptide comprises a residue comprising from 20 to about 60 amino acids, including six cysteine residues. The cysteine residues form disulfide bonds which cause the peptide residue to have a clover-like shape comprising three loops. The methods of preparing of TFF-peptides, such as recombinant expression of peptides and synthetic peptide synthesis, are well known in the art. For example, methods of preparing TFF-peptides are included in the following references: U.S. Pat. No. 6,525,018; Allen, et. al., *J Clin Gastroenterol* 1998; 10 (Suppl 1): S93-S98; Ligumsky, et. al., *Isr J Med Sci* 1986; 22:801-806;

Dignass, et. al., *J. Clin. Invest.*, 94, 376-383; Babyatsky, et. al., *Gastroenterology*, 110, 489-497; Hauser, et. al., *Proc. Natl. Acad. Sci. USA*, vol. 90, pp. 6961-6965, August 1993; WO 02102403; and WO02085402, incorporated herein by reference. In one embodiment the trefoil factor family peptide is TFF1, TFF2, or TFF3. In another embodiment the trefoil factor family peptide is TFF1 or TFF3.

The concentration or amount of the trefoil factor family peptide used in the methods and compositions disclosed herein can readily be determined by one of ordinary skill in the art without undue experimentation. In one embodiment, the concentration of the trefoil factor family peptide is from 0.001% to 1%. In another embodiment, the concentration of the trefoil factor family peptide is from 0.01% to 0.5%. In another embodiment, the concentration of the trefoil factor family peptide is from 0.1% to 0.2%. In another embodiment, the concentration of the trefoil factor family peptide is about 0.15%.

A mucoadhesive is used in certain of the compositions and methods disclosed herein. With respect to this invention, the term "mucoadhesive" means a natural or synthetic component, including macromolecules, polymers, and oligomers, or mixtures thereof, that can adhere to a subject's mucous membrane. Adhesion of mucoadhesives to the mucous membrane occurs primarily through noncovalent interactions, such as hydrogen bonding and Van der Waal forces (Tabor et al., 1977 J. Colloid Interface Sci. 58:2 and Good 1977 J. Colloid Interface Sci. 59:398). Examples of mucoadhesives for use in the embodiments disclosed herein include, but are not limited to, Carbopol®, pectin, alginic acid, alginate, chitosan, hyaluronic acid, polysorbates, such as polysorbate-20, -21, -40, -60, -61, -65, -80, -81, -85; poly(ethyleneglycol), such as PEG-7, -14, -16, -18, -55, -90, -100, -135, -180, -4, -240, -6, -8, -9, -10, -12, -20, or -32; oligosaccharides and polysaccharides, such as Tamarind seed polysaccharide, gellan, carrageenan, xanthan gum, gum Arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethyleneoxide) with various reactive hydrogen containing compounds having long hydrophobic chains (e.g. aliphatic chains of about 12 to 20 carbon atoms), for example, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide; mixtures of block copolymers of ethylene oxide and propylene oxide with other excipients, for example poly(vinyl alcohol); polyacrylamide; hydrolyzed polyacrylamide; poly(vinyl pyrrolidone); poly(methacrylic acid); poly(acrylic acid) or crosslinked polyacrylic acid, such as Carbomer®, i.e., a homopolymer of acrylic acid crosslinked with either an allyl ether of pentaerythritol, an allyl ether of sucrose, or an allyl ether of propylene. In certain embodiments the mucoadhesive is a polysaccharide. One polysaccharide which is particularly useful as a mucoadhesive in the embodiments disclosed herein is Tamarind seed polysaccharide, which is a galactoxyloglucan that is extracted from the seed kernel of *Tamarindus Indica*, and can be purchased from TCI America of Portland, Oreg.

In certain embodiments a buffer is included to maintain the pH from about 6 to about 8. In particular cases, it is desirable to maintain the pH about 7. Buffers used are those known to those skilled in the art, and, while not intending to be limiting, some examples are acetate, borate, carbonate, citrate, and phosphate buffers. Preferably, the buffer comprises borate. An effective amount of buffer necessary for the purposes of this invention can be readily determined by a person skilled in the art without undue experimentation. In certain embodiments where the buffer comprises borate, the concentration of the borate buffer is about 0.6%.

In any of the compositions described herein, a tonicity agent may be used. Tonicity agents are used in ophthalmic compositions to adjust the concentration of dissolved material to the desired isotonic range. Tonicity agents are known to those skilled in the ophthalmic art, and, while not intending to be limiting, some examples include glycerin, mannitol, sorbitol, sodium chloride, and other electrolytes. On particularly useful tonicity agent is sodium chloride.

In any of the compositions are described herein, a preservative may be used, particularly when the composition is intended for multiple use. There may also be reasons to use a preservative in single use compositions depending on the individual circumstances. The term preservative has the meaning commonly understood in the ophthalmic art. Preservatives are used to prevent bacterial contamination in multiple-use ophthalmic preparations, and, while not intending to be limiting, examples include benzalkonium chloride, stabilized oxychloro complexes (otherwise known as Purite®), phenylmercuric acetate, chlorobutanol, benzyl alcohol, parabens, and thimerosal. One particularly useful preservative is benzalkonium chloride (BAK).

Under certain circumstances, a surfactant might be used in any of the compositions related to this invention which are described herein. The term surfactant used herein has the meaning commonly understood in the art. Surfactants are used to help solubilize the therapeutically active agent or other insoluble components of the composition, and may serve other purposes as well. Anionic, cationic, amphoteric, zwitterionic, and nonionic surfactants may all be used in this invention. Nonionic surfactants, such as polysorbates, poloxamers, alcohol ethoxylates, ethylene glycol-propylene glycol block copolymers, fatty acid amides, alkylphenol ethoxylates, or phospholipids, are particularly useful for the compositions and methods disclosed herein.

Another type of compound that might be used in any composition described herein is a chelating agent. The term chelating agent refers to a compound that is capable of complexing a metal, as understood by those of ordinary skill in the chemical art. Chelating agents are used in ophthalmic compositions to enhance preservative effectiveness. While not intending to be limiting, some useful chelating agents are edetate salts, like edetate disodium, edetate calcium disodium, edetate sodium, edetate trisodium, and edetate dipotassium.

One particularly useful embodiment comprises a prostaglandin-related compound at a concentration from 0.001% to 0.1%, a trefoil factor family peptide, tamarind seed polysaccharide, about 0.5% sodium chloride, about 0.005% benzalkonium chloride, and about 0.6% of a borate buffer wherein the pH of the composition is adjusted to from about 6 to about 8. In one composition, the prostaglandin-related compound is bimatoprost, which is present at a concentration of 0.03%. In another composition, the prostaglandin-related compound is latanoprost, which is present at a concentration of 0.005%. In another composition, the prostaglandin-related compound is travoprost, which is present at a concentration of 0.004%. In another composition, the prostaglandin-related compound is unoprostone isopropyl, which is present at a concentration of 0.15%.

Another embodiment relates to a pharmaceutical product comprising a composition comprising a therapeutically effective amount of a prostaglandin F-related compound and a therapeutically effective concentration of a trefoil factor family peptide, and a package suitable for ophthalmic use from which said composition is dispensed, wherein the use of the composition for the prevention or treatment of glaucoma is indicated thereon.

The best mode of making and using the present invention are described in the following examples. These examples are given only to provide direction and guidance in how to make and use the invention, and are not intended to limit the scope of the invention in any way.

EXAMPLE 1

Compositions related to this invention are prepared by the following procedure. Unless otherwise indicated, all procedural steps are carried out at room temperature.

Part I

Tamarind seed polysaccharide (TSP) is added to purified water at the concentration indicated in the Table 1, and the solution is brought to a boil and maintained at a gentle boil for about 30 minutes. The solution is then allowed to cool to room temperature, and water is added to compensate for evaporative loss during boiling. The solution is then filtered through a 20 micron clarity filter followed by a 0.45 micron sterilizing filter.

Part II

Each component listed in Table 1 is added in amount needed to provide the indicated concentration to a fixed volume of the solution from part I, in the following order: TFF 1, boric acid, sodium borate decahydrate, sodium chloride, and BAK. After the addition of each component, the mixture is stirred until the solute is completely dissolved before the next component is added. When all of the components of the formulation have been added and dissolved, the pH is then adjusted to 7.0 with NaOH or HCl. The solution is then sterile filtered.

TABLE 1

| Component | Function | % (w/v) |
|---|---|---|
| Bimatoprost | Prostamide | 0.03 |
| TFF 1 | TFF-peptide | 0.15 |
| Tamarind Seed Polysaccharide (TSP) | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Preservative | 0.005 |
| Purified Water | | Q.s. |
| HCl or NaOH | Buffer | adjust to pH 7.0 |

EXAMPLE 2

A formulation having the composition of Table 2 is prepared according to an analogous procedure to that of Example 1. Latanoprost is well known in the art, and can be prepared by procedures described in U.S. Pat. No. 6,429,226, incorporated herein by reference.

TABLE 2

| Component | Function | % (w/v) |
|---|---|---|
| Latanoprost | Prostaglandin | 0.005 |
| TFF 1 | TFF-peptide | 0.15 |
| Tamarind Seed Polysaccharide (TSP) | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Preservative | 0.005 |
| Purified Water | | Q.s. |
| HCl or NaOH | Buffer | adjust to pH 7.0 |

EXAMPLE 3

A formulation having the composition of Table 3 is prepared according to an analogous procedure to that of Example 1.

TABLE 3

| Component | Function | % (w/v) |
|---|---|---|
| Bimatoprost | Prostamide | 0.03 |
| TFF 1 | TFF-peptide | 0.15 |
| Sodium Carboxymethylcellulose | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Preservative | 0.005 |
| Purified Water | | Q.s. |
| HCl or NaOH | Buffer | adjust to pH 7.0 |

EXAMPLE 4

A formulation having the composition of Table 4 is prepared according to an analogous procedure to that of Example 1.

TABLE 4

| Component | Function | % (w/v) |
|---|---|---|
| Bimatoprost | Prostamide | 0.03 |
| TFF 3 | TFF-peptide | 0.15 |
| Hydroxypropylmethylcellulose | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Preservative | 0.005 |
| Purified Water | | Q.s. |
| HCl or NaOH | Buffer | adjust to pH 7.0 |

EXAMPLE 5

A formulation having the composition of Table 5 is prepared according to an analogous procedure to that of Example 1.

TABLE 5

| Component | Function | % (w/v) |
|---|---|---|
| Bimatoprost | Prostamide | 0.03 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Preservative | 0.005 |
| Purified Water | | Q.s. |
| HCl or NaOH | Buffer | adjust to pH 7.0 |

EXAMPLE 6

A formulation having the composition of Table 6 is prepared according to an analogous procedure to that of Example 1.

TABLE 6

| Component | Function | % (w/v) |
|---|---|---|
| Travoprost | Prostaglandin | 0.004 |
| TFF 1 | TFF-peptide | 0.15 |
| Sodium Carboxymethylcellulose | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Preservative | 0.005 |
| Purified Water | | Q.s. |
| HCl or NaOH | Buffer | adjust to pH 7.0 |

EXAMPLE 7

A formulation having the composition of Table 7 is prepared according to an analogous procedure to that of Example 1.

TABLE 7

| Component | Function | % (w/v) |
|---|---|---|
| Unoprostone isopropyl | Prostamide | 0.15% |
| TFF 3 | TFF-peptide | 0.15 |
| Hydroxypropylmethylcellulose | Mucoadhesive | 0.5 |
| Boric Acid | Buffer | 0.6 |
| Sodium Borate Decahydrate | Buffer | 0.035 |
| Sodium Chloride | Tonicity Agent | 0.53 |
| Benzalkonium Chloride (BAK) | Preservative | 0.005 |
| Purified Water | | Q.s. |
| HCl or NaOH | Buffer | adjust to pH 7.0 |

EXAMPLE 8

A drop of a composition prepared according to one of Examples 1 and 3-5 is added at least once a day to several patients suffering from glaucoma. Reduction in intraocular pressure is observed for all patients, but with reduced hyperemia observed in the patients receiving the compositions of Examples 1, 3 and 4, which have a trefoil factor family peptide, relative to the patients receiving the composition of Example 5.

What is claimed is:

1. A dosage form comprising a prostamide and a trefoil factor family peptide wherein the prostamide is bimatoprost and the peptide is selected form the group consisting of TFF1 and TFF3.

2. The dosage form of claim 1 wherein the concentration of the prostamide is from 0.001% to 0.1%.

3. The dosage form of claim 1 wherein the concentration of the trefoil factor family peptide is from 0.001% to 1%.

4. The dosage form of claim 1 wherein the concentration of the trefoil factor family peptide is from 0.01% to 0.5%.

5. The dosage form of claim 1 wherein the concentration of the trefoil factor family peptide is from 0.1% to 0.2%.

6. The dosage form of claim 1 wherein the concentration of the trefoil factor family peptide is about 0.15%.

7. The dosage form of claim 1 which further comprises a mucoadhesive.

8. The dosage form of claim 1 which further comprises a polysaccharide.

9. The dosage form of claim 1 which further comprises Tamarind seed polysaccharide.

10. The dosage form of claim 1 wherein the trefoil family factor peptide is TFF3.

11. The dosage form of claim 1 wherein the trefoil family factor peptide is TFF1.

12. The dosage form of claim 2 which comprises Tamarind seed polysaccharide, about 0.5% sodium chloride, about 0.005% benzalkonium chloride, and about 0.6% of a borate buffer wherein the pH of the composition is adjusted to from about 6 to about 8.

13. The dosage form of claim 12 which comprises about 0.03% bimatoprost.

14. A pharmaceutical composition for treatment of glaucoma comprising a composition comprising a therapeutically effective amount of prostamide and a therapeutically effective amount of trefoil factor family peptide wherein the prostamide is bimatoprost and the peptide is selected from the group consisting of TFF1 and TFF3.

* * * * *

UNITED STATES PATENT AND TRADEMARK OFFICE
CERTIFICATE OF CORRECTION

PATENT NO. : 7,244,768 B2
APPLICATION NO. : 10/521367
DATED : July 17, 2007
INVENTOR(S) : Bakhit et al.

It is certified that error appears in the above-identified patent and that said Letters Patent is hereby corrected as shown below:

On the Title page, in Item (75), in "Inventors", in column 1, line 1, delete "Bech," and insert -- Beach, --, therefor.

On the Title page, in Item (56), under "Other Publications", in column 2, line 8, delete "polysccharide" and insert -- polysaccharide --, therefor.

On the Title page, in Item (56), under "Other Publications", in column 2, line 15, delete "Biorganic" and insert -- Bioorganic --, therefor.

On the Title page, in Item (56), under "Other Publications", in column 2, line 25, delete "Epitheal" and insert -- Epithelial --, therefor.

On the Title page, in Item (56), under "Other Publications", in column 2, line 34, delete "Gastronenterol," and insert -- Gastroenterol, --, therefor.

On the Title page, in Item (56), under "Other Publications", in column 2, line 44, delete "Collioid" and insert -- Colloid --, therefor.

In column 2, line 56, delete ""Synethesis" and insert -- "Synthesis --, therefor.

In column 3, line 54, delete "vol" and insert -- vol. --, therefor.

In column 3, lines 66-67, delete "epithelial-cells" and insert -- epithelial cells --, therefor.

In column 7, line 11, delete "[$^3$H]-" and insert -- [$^3$H-] --, therefor.

In column 7, line 52, delete "U46619" and insert -- U-46619 --, therefor.

In column 9, line 4, delete "WO02085402," and insert -- WO 02085402, --, therefor.

In column 14, line 8, in Claim 1, delete "form" and insert --from --, therefor.

UNITED STATES PATENT AND TRADEMARK OFFICE
CERTIFICATE OF CORRECTION

PATENT NO. : 7,244,768 B2
APPLICATION NO. : 10/521367
DATED : July 17, 2007
INVENTOR(S) : Bakhit et al.

It is certified that error appears in the above-identified patent and that said Letters Patent is hereby corrected as shown below:

In column 14, line 30, in Claim 12, after "which" insert -- further --.

Signed and Sealed this

Eighteenth Day of December, 2007

JON W. DUDAS
*Director of the United States Patent and Trademark Office*